United States Patent [19]

Lafferty et al.

[11] Patent Number: 4,963,547
[45] Date of Patent: Oct. 16, 1990

[54] ALPHA-ANDRENERGIC RECEPTOR ANTAGONISTS AND USE THEREAS

[75] Inventors: John J. Lafferty, Levittown; Robert M. Demarinis, Ardmore; Dinubhai H. Shah, Norristown, all of Pa.

[73] Assignee: SmithKline Beecham Corporation, Philadelphia, Pa.

[21] Appl. No.: 362,121

[22] Filed: Jun. 6, 1989

Related U.S. Application Data

[63] Continuation-in-part of Ser. No. 201,004, Jun. 1, 1988, abandoned.

[51] Int. Cl.$^5$ .................... C07D 495/06; A61K 31/38
[52] U.S. Cl. ..................... 514/217; 590/581; 590/586; 590/542; 514/81
[58] Field of Search ................ 540/581, 542; 514/217, 514/81

[56] References Cited

U.S. PATENT DOCUMENTS

| | | | |
|---|---|---|---|
| 3,649,644 | 3/1972 | Sountag et al. | 540/581 |
| 3,833,591 | 9/1974 | McManus | 260/239 R |
| 3,856,910 | 12/1974 | Medelec et al. | 514/215 |
| 3,904,645 | 9/1975 | McManus | 260/326.5 B |
| 3,906,000 | 9/1975 | McManus | 260/326.5 B |
| 4,469,634 | 9/1984 | DeMarinis | 262/239 BB |
| 4,769,368 | 9/1988 | Kaiser et al. | 514/217 |
| 4,833,249 | 5/1989 | Kosley et al. | 540/581 |

FOREIGN PATENT DOCUMENTS

| | | | |
|---|---|---|---|
| 2194786 | 3/1988 | European Pat. Off. | 540/581 |
| 0144286 | 9/1982 | Japan | 514/217 |
| 8700522 | 1/1987 | PCT Int'l Appl. | |

Primary Examiner—David B. Springer
Attorney, Agent, or Firm—Mary E. McCarthy; Stuart R. Suter; Edward T. Lentz

[57] ABSTRACT

Alpha-adrenoceptor antagonists having the formula:

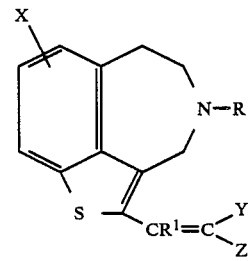

which are useful to produce α-adrenoceptor antagonism, pharmaceutical compositions including these antagonists, and methods of using these antagonists to produce α-adrenoceptor antagonism in mammals.

16 Claims, No Drawings

ALPHA-ANDRENERGIC RECEPTOR ANTAGONISTS AND USE THEREAS

This application is a continuation-in-part of U.S. Ser. No. 07/201,004, filed on June 1, 1988, abandoned.

FIELD OF THE INVENTION

This invention relates to novel substituted-2-ethenyl-3,4,5,6-tetrahydrothieno[4,3,2-ef][3]benzazepine compounds that are α-adrenergic receptor antagonists.

BACKGROUND OF THE INVENTION

The autonomic nervous system is separated into the cholinergic and adrenergic nervous systems. Norepinephrine, the neurotransmitter of the adrenergic nervous system, exerts its activity by interaction with receptors (adrenoceptors) on the effector organs or on the nerve endings. The adrenoceptors are of two primary types: α and β. Based upon selectivity of the receptors for a series of agonists and antagonists, the α adrenoceptors have been subdivided into $\alpha_1$ and $\alpha_2$ subtypes.

A large amount of experimental evidence now supports the view that the $\alpha_2$ subtype is a heterogeneous adrenoceptor class. (For a general review see Timmermans and Van Zwieten, *J. Med. Chem.*, 25, 1389 (1982)). Experiments using 6-chloro-9-(3-methyl-2-butenyloxy)-3-methyl-2,3,4,5-tetrahydro-1H-3-benzazepine (SK&F 104078) demonstrated that the classical adrenoceptors are heterogeneous and can be divided into SK&F 104078—insensitive and SK&F 104078—sensitive $\alpha_2$ adrenoceptors. The latter variously are referred to as postjunctional $\alpha_2$ adrenoceptors or, preferably, $\alpha_3$ adrenoceptors, U.S. Pat. No. 4,683,229, July 28, 1987.

As one of the primary regulators of peripheral vascular tone, α adrenoceptors long have been the targets of efforts to develop agents effective in changing vascular tone for use in treating diseases, such as hypertension, in which alterations in vascular resistance produce therapeutic benefits. Antihypertensive compounds presently in clinical use that function via interaction with α adrenoceptors include methyldopa, clonidine, and prazosin. Efforts to modulate sympathetic tone through interactions with α adrenoceptors have resulted in several compounds that interact somewhat selectively with $\alpha_1$ or $\alpha_2$ adrenoreceptors. Selective agonists include phenylephrine and methoxamine which preferentially activate $\alpha_1$ receptors; and clonidine, α-methylnorepinephrine, and tramazoline which preferentially activate $\alpha_2$ adrenoceptors. Examples of selective α-adrenoceptor antagonists include prazosin which has high selectivity for $\alpha_1$ adrenoceptors; and the $\alpha_2$-selective blockers yohimbine and rauwolscine.

U.S. Pat. No. 4,469,634, dated Sept. 4, 1984, describes allyloxy- and allylthio-2,3,4,5-tetrahydro-1H-3-benzazepines useful as intermediates for preparing $\alpha_2$ adrenoceptor affinity resins and as antihypertensive agents.

U.S. Pat. Nos. 3,833,591, 3,904,645, and 3,906,000 disclose substituted compounds of the following base structure:

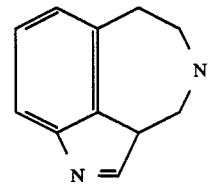

These compounds are useful as hypoglycemic agents.

PCT Application Number WO No. 0 87/00522 describes a series of 4-aminotetrahydrobenz[c,d]indoles and tetrahydroazepino[3,4,5-c,d]indoles having the general formula:

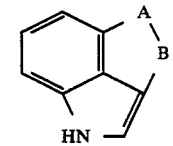

in which A—B is —CH$_2$—CH(NRR)—CH$_2$ or —CH$_2$—CH$_2$—NR—CH$_2$. These compounds are dopamine agonists useful as hypotensives.

SUMMARY OF THE INVENTION

The present invention resides in the discovery that various substituted-2-ethenyl-3,4,5,6-tetrahydrothieno[4,3,2-ef][3]benzazepine compounds are α-adrenoceptor antagonists. Presently preferred compounds of the invention include:

7-chloro-2-ethenyl-3,4,5,6-tetrahydro-4-methyl-thieno[4,3,2-ef][3]benzazepine;

ethyl (E)-3-(7-chloro-3,4,5,6-tetrahydro-4-methyl-thieno[4,3,2-ef][3]benzazepin-2-yl)-2-propenoate;

ethyl (E)-3-(7-chloro-3,4,5,6-tetrahydro-4-methyl-thieno[4,3,2-ef][3]benzazepin-2-yl)-2-methyl-2-propenoate;

(E)-3-(7-chloro-3,4,5,6-tetrahydro-4-methyl-thieno[4,3,2-ef][3]benzazepin-2-yl)-2-propenamide;

(E)-3-(7-chloro-3,4,5,6-tetrahydro-4-methyl-thieno[4,3,2-ef][3]benzazepin-2-yl)-N-methyl-2-propenamide;

(E)-3-(7-chloro-3,4,5,6-tetrahydro-4-methyl-thieno[4,3,2-ef][3]benzazepin-2-yl)-N,N-dimethyl-2-propenamide;

(E)-3-(7-chloro-3,4,5,6-tetrahydro-4-methyl-thieno[4,3,2-ef][3]benzazepin-2-yl)-2-propen-1-ol;

7-chloro-2-ethenyl-3,4,5,6-tetrahydrothieno[4,3,2-ef][3]benzazepine;

ethyl (E/Z)-(7-chloro-3,4,5,6-tetrahydro-4-methyl-thieno[4,3,2-ef][3]benzazepin-2-yl)-2-phenyl-2-propenoate;

(E)-3-(7-chloro-3,4,5,6-tetrahydro-4-methyl-thieno[4,3,2-ef][3]benzazepin-2-yl)-2-phenyl-2-propenenitrile;

7-chloro-3,4,5,6-tetrahydro-4-methyl-2-(1-methylethenyl)thieno[4,3,2-ef][3]benzazepine; and 7-chloro-2-propenyl-3,4,5,6-tetrahydrothieno[4,3,2-ef][3]benzazepine;

or a pharmaceutically acceptable salt thereof.

In a further aspect of the invention there are provided methods of antagonizing α adrenoceptors in mammals, including humans, that comprise administering internally to a subject in need of such antagonism an effective amount of a substituted-2-ethenyl-3,4,5,6-tetrahydrothieno[4,3,2-ef][3]benzazepine compound.

Included in the present invention are pharmaceutical compositions that include compounds useful in the method of the invention and a suitable pharmaceutical carrier. Preferably, these compositions are used to produce α-adrenoceptor antagonism and contain an effective amount of compounds useful in the methods of the invention.

DETAILED DESCRIPTION OF THE INVENTION

The presently invented compounds that are α-adrenoceptor antagonists are represented by the following Formula (I):

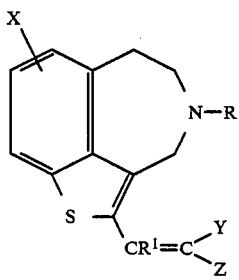

in which:

X is H, Cl, Br, F, I, $CF_3$, $C_{1-6}$alkyl, $COR^{10}$, $CO_2R^{10}$, $CONR^{16}R^{11}$, CN, $NO_2$, $NR^{12}R^{13}$, $OR^{12}$, $SC_{1-4}$alkyl, $S(CH_2)_{0-6}$aryl, $SCF_3$, or any accessible combination thereof of up to three substituents;

R is H, $C_{1-6}$alkyl, or $C_{3-5}$alkenyl;

$R^1$ is H or $C_{1-6}$alkyl;

$R^{10}$ is $C_{1-6}$alkyl or $(CH_2)_{0-6}$aryl;

$R^{11}$ and $R^{16}$ independently are H, $C_{1-6}$alkyl, or $(CH_2)_{0-6}$aryl;

$R^{12}$ is H, $C_{1-6}$alkyl, $COR^{14}$, or $SO_2R^{15}$;

$R^{13}$ is H or $C_{1-6}$alkyl;

$R^{14}$ and $R^{15}$ independently are $C_{1-6}$alkyl or $(CH_2)_{0-6}$aryl;

Y and Z independently are H, $NO_2$, $C_{1-6}$alkyl, $CH_2CH_2OH$, CN, $CH_2OR^2$, $CH_2SR^2$, $COR^2$, $CO_2R^2$, $CONR^3R^4$, $SO_2NR^3R^4$, $SO_3R^2$, $SO_2R^5$, $SOR^5$, $P(O)(OR^3)(OR^4)$, $P(O)R^5(OR^3)$, $P(O)R^5R^6$, $P(O)(OR^2)NR^3R^4$, $P(O)(NR^3R^4)_2$, $P(O)R^5(NR^3R^4)$, halo, $CF_3$, or $(CH_2)_{0-6}$aryl;

$R^2$, $R^3$, and $R^4$ independently are H, $C_{1-6}$alkyl, $C_{3-5}$alkenyl, or $(CH_2)_{0-6}$aryl; and $R^5$ and $R^6$ independently are $C_{1-6}$alkyl, $C_{3-5}$alkenyl, or $(CH_2)_{0-6}$aryl; or a pharmaceutically acceptable salt thereof.

As used herein $C_{1-6}$alkyl means straight or branched alkyl of one to six carbon atoms, $C_{3-5}$alkenyl means a straight or branched chain alkenyl having from 3 to 5 carbon atoms, aryl means a phenyl group which is unsubstituted or is substituted once or twice by $C_{1-6}$alkyl, $C_{1-6}$alkoxy, halo, $CF_3$, or CN, and "any accessible combination thereof" means any combination of up to three substituents on the phenyl moiety that is available by chemical synthesis and is stable.

Formula (Ia) includes presently preferred Formula (I) compounds:

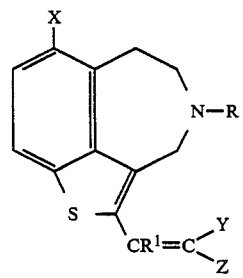

in which:

X is H, Cl, Br, F, I, $CF_3$, $C_{1-6}$alkyl, $COR^{10}$, $CO_2R^{10}$, $CONR^{16}R^{11}$, CN, $NO_2$, $NR^{12}R^{13}$, $OR^{12}$, $SC_{1-4}$alkyl, $S(CH_2)_{0-6}$aryl, or $SCF_3$;

R is H, $C_{1-6}$alkyl, or $C_{3-5}$alkenyl;

$R^1$ is H or $C_{1-6}$alkyl;

$R^{10}$ is $C_{1-6}$alkyl or $(CH_2)_{0-6}$aryl;

$R^{11}$ and $R^{16}$ independently are H, $C_{1-6}$alkyl, or $(CH_2)_{0-6}$aryl;

$R^{12}$ is H, $C_{1-6}$alkyl, $COR^{14}$, or $SO_2R^{15}$;

$R^{13}$ is H or $C_{1-6}$alkyl;

$R^{14}$ and $R^{15}$ independently are $C_{1-6}$alkyl or $(CH_2)_{0-6}$aryl;

Y and Z independently are H, $NO_2$, $C_{1-6}$alkyl, $CH_2CH_2OH$, CN, $CH_2OR^2$, $CH_2SR^2$, $COR^2$, $CO_2R^2$, $CONR^3R^4$, $SO_2NR^3R^4$, $SO_3R^5$, $SO_2R^5$, $SOR^5$, $P(O)(OR^3)(OR^4)$, $P(O)R^5(OR^3)$, $P(O)R^5R^6$, $P(O)(OR^2)NR^3R^4$, $P(O)(NR^3R^4)_2$, $P(O)R^5(NR^3R^4)$, halo, $CF_3$, or $(CH_2)_{0-6}$aryl;

$R^2$, $R^3$, and $R^4$ independently are H, $C_{1-6}$alkyl, $C_{3-5}$alkenyl, or $(CH_2)_{0-6}$aryl; and $R^5$ and $R^6$ independently are $C_{1-6}$alkyl, $C_{3-5}$alkenyl, or $(CH_2)_{0-6}$aryl; or a pharmaceutically acceptable salt thereof.

Compounds of Formula (I) are prepared by the synthetic pathways shown in Schemes I through III. In Schemes I through III, $R^3$, $R^4$, X, Y, and Z are as defined in Formula (I).

SCHEME I

Method A

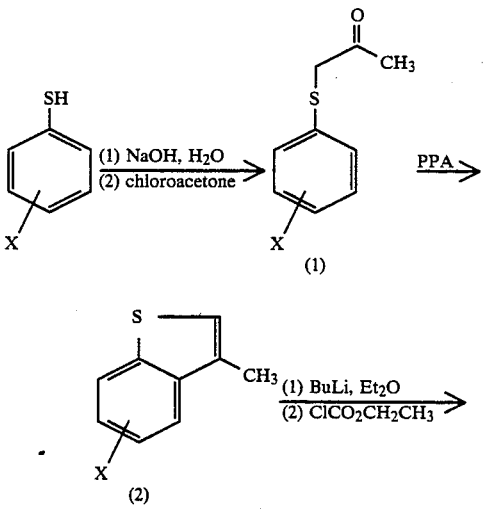

-continued
SCHEME I
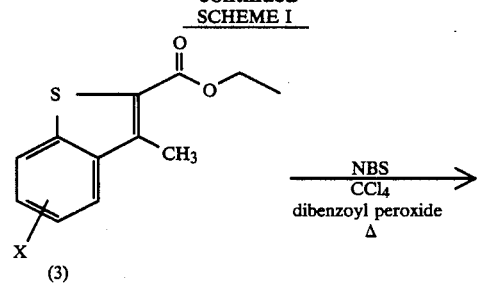
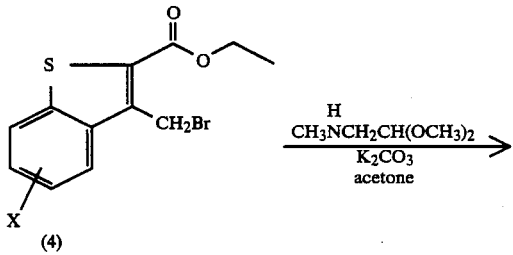
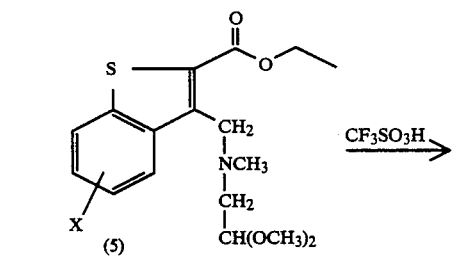
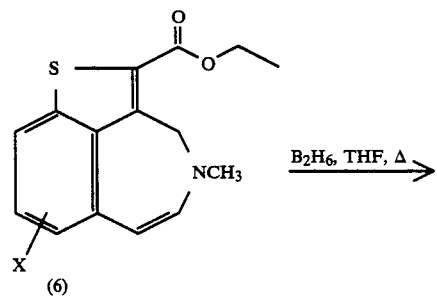
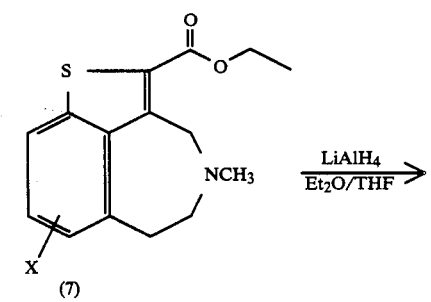
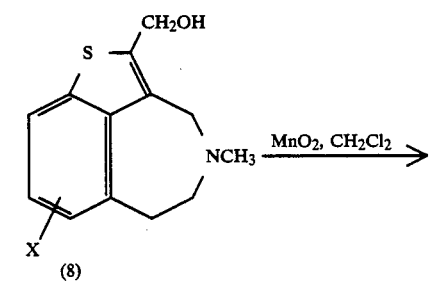
-continued
SCHEME I
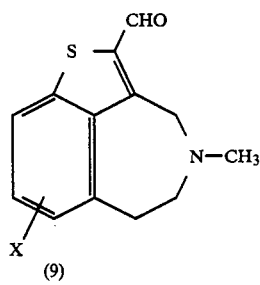
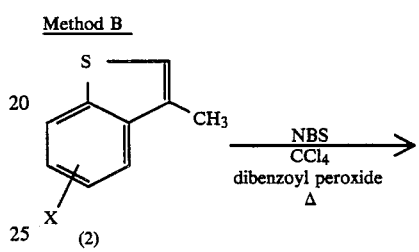
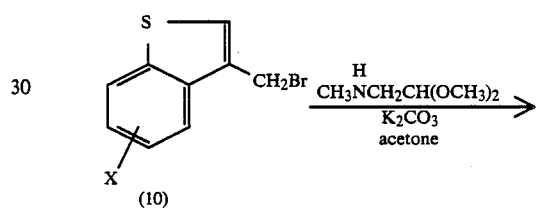
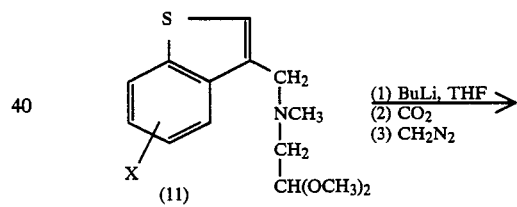
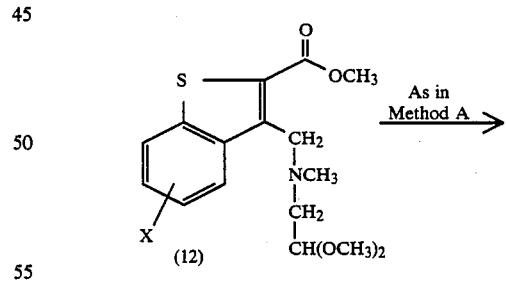
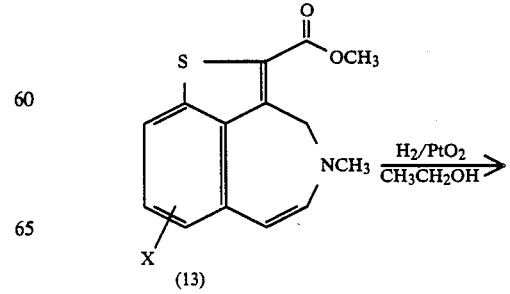

-continued
SCHEME I

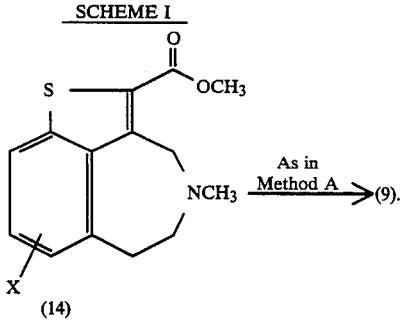

Scheme I, Method A, shows the synthesis of Formula (I) related compounds in which the 2-position substituent is $CO_2CH_2CH_3$, CHO, and $CH_2OH$, which are useful as intermediates in synthesis of Formula (I) compounds. According to Scheme I, thiophenol or a substituted thiophenol is treated with a base such as sodium hydroxide in a suitable solvent such as water The resulting sodium thiophenolates are heated at 0° C. to 75° C., preferably 25° C., with a haloacetone, preferably chloroacetone to yield (phenylthio)propanones (1). Substituted benzo[b]thiophene formula (2) compounds are prepared by treating formula (1) compounds with a strong acid, preferably polyphosphoric acid (PPA), at from 0° C. to 175° C., preferably 25° C. to 130° C.

Formula (2) compounds are treated with a strong base, preferably butyllithium, in an inert solvent, preferably ethyl ether, at a suitable temperature, preferably 0° C., and then with an alkyl chloroformate, preferably ethyl chloroformate, at a suitable temperature, preferably 0° C., to produce formula (3) compounds.

Formula (3) compounds are treated with a halogenating agent, preferably N-bromosuccinimide (NBS), and an initiator, preferably dibenzoylperoxide, in an inert organic solvent, preferably carbon tetrachloride ($CCl_4$), preferably at reflux, to produce formula (4) compounds. Formula (5) compounds are prepared by dissolving formula (4) compounds in an organic solvent such as acetone and adding a suitable base, preferably potassium carbonate ($K_2CO_3$), and an N-($C_{1-6}$alkyl)-aminoacetaldehyde di($C_{1-4}$alkyl) acetal, preferably methylaminoacetaldehyde dimethyl acetal.

Formula (5) compounds are treated with acid, preferably trifluoromethanesulfonic acid, to yield enamine compounds of formula (6). Formula (6) compounds are treated with a reducing agent, preferably diborane, in an inert organic solvent such as tetrahydrofuran at a suitable temperature, such as at reflux, or reduced catalytically with a suitable catalyst, preferably platinum oxide, in a suitable solvent, preferably ethanol, to give benzazepine compounds of formula (7).

Thereafter, formula (7) compounds are added to a suitable reducing agent, preferably lithium aluminum hydride (LAH), in an inert solvent, preferably ethyl ether, to yield formula (8) compounds. Formula (8) compounds are treated with a suitable oxidizing agent, preferably manganese dioxide, in an inert solvent, preferably dichloromethane, to give benzazepine-2-carboxaldehyde compounds of formula (9).

Scheme I, Method B, shows an alternative synthesis of Formula (I) related compounds in which the 2-position substituent is $CO_2CH_3$. Formula (2) compounds are treated with a halogenating agent, preferably N-bromosuccinimide (NBS), and an initiator, preferably dibenzoylperoxide, in an inert organic solvent, preferably carbon tetrachloride ($CCl_4$), preferably at reflux, to produce formula (10) compounds.

Formula (11) compounds are prepared by dissolving formula (10) compounds in an organic solvent such as acetone and adding a suitable base, preferably potassium carbonate ($K_2CO_3$), and an N-($C_{1-6}$alkyl)-aminoacetaldehyde di($C_{1-4}$alkyl) acetal, preferably methylaminoacetaldehyde dimethyl acetal.

Formula (11) compounds are treated with a strong base, preferably butyllithium, in an inert solvent, preferably ethyl ether, at a suitable temperature, preferably −30° C., and then with carbon dioxide to produce carboxylic acids which are treated with an alkylating agent, such as diazomethane, in an inert solvent, such as ethyl ether, to give formula (12) compounds.

Formula (12) compounds are converted to formula (13), formula (14), formula (8) and formula (9) compounds as described for Method A.

SCHEME II

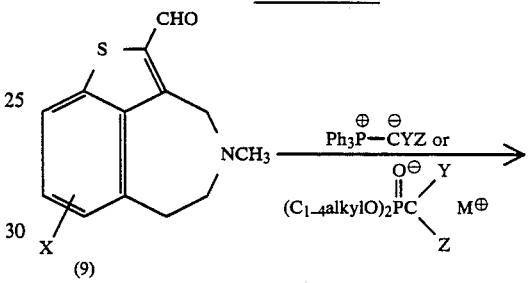

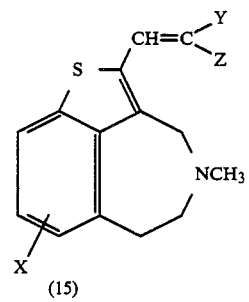

Scheme II shows formation of formula (15) compounds which are Formula (I) compounds except those in which the 2-position substituent is —CH=CH—CHO, —CH=CH—COOH, or —CH=CHCONR³R⁴. In Scheme II, X is as defined in Formula (I). The starting compounds in Scheme II are formula (9) benzazepine-2-carboxaldehydes prepared as in Scheme I. According to Scheme II, the formula (9) compound is reacted with a phosphonate or phosphonium salt in the presence of a suitable base, preferably sodium hydride, except when Y or Z is $SO_2NR^3R^4$ wherein sodium methoxide is preferred. The phosphonate or phosphonium salt is selected so that Y and Z are the same as in the desired Formula (I) compound. The metal cation ($M^\ominus$) associated with the phosphonate is derived from the base employed in this step of the synthesis. Suitable metal ions include lithium, sodium, and potassium.

Formula (I) compounds wherein the 2-position substituent is CH=CH—CHO are prepared by a process similar to Scheme II by reacting the formula (9) compound with a dialkyl phosphonoacetaldehyde dialkyl acetal, preferably diethyl phosphonoacetaldehyde diethyl acetal, followed by acid hydrolysis.

SCHEME III

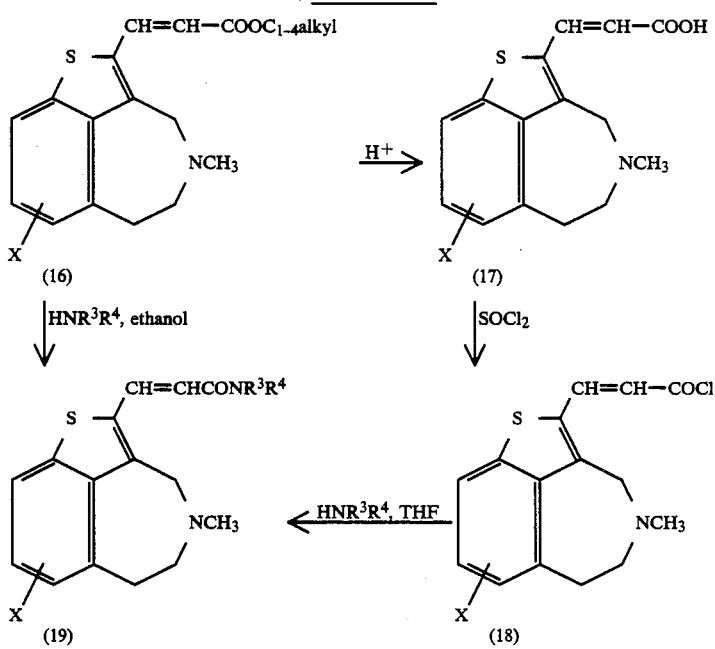

Scheme III outlines synthesis of Formula (I) compounds wherein the 2-position substituent is CH=CH—COOH or CH=CHCONR$^3$R$^4$. The formula (16) starting materials in the Scheme III process are prepared according to Scheme II and are included within the formula (15) compounds. Formula (17) compounds are formed by adding strong acid, preferably a mixture of hydrochloric and acetic acids, to formula (16) compounds and heating the mixture to approximately 30° C. to 70° C., Preferably 50° C. Compounds of formula (18) then are prepared by reacting the formula (17) compounds with a suitable halogenating agent, preferably thionyl chloride. Formula (19) compounds, which are Formula (I) compounds wherein Y or Z is CONR$^3$R$^4$ are synthesized by reacting formula (18) compounds with ammonia or substituted amines wherein R$^3$ and R$^4$ are as in the desired Formula (I) compound. Alternatively, formula (19) compounds are prepared by reacting the formula (16) esters with ammonia or a substituted amine.

Formula (I) compounds wherein R$^1$ is C$_{1-6}$alkyl are prepared by reacting formula (7) or formula (14) compounds with a C$_{1-6}$alkylmagnesium halide, such as methylmagnesium bromide, in a suitable solvent, such as tetrahydrofuran, followed by reaction with methanesulfonyl chloride in the presence of a suitable base, such as triethylamine.

Schemes I through III outline preparation of Formula (I) compounds in which R is methyl. Formula (I) compounds wherein R is other than methyl are formed by selecting the N-(C$_{1-6}$alkyl)aminoacetaldehyde di(C$_{1-4}$alkyl) acetal used in preparing the formula (5) and (11) compounds of Scheme I so that the nitrogen is desirably substituted. Alternatively, Formula (I) compounds wherein R is other than methyl are prepared by reacting a Formula (I) compound wherein R is methyl with an alkyl haloformate, preferably trichloroethyl chloroformate at approximately 50° C. to 100° C. to produce a trihaloalkyl carbamate. To this carbamate dissolved in a suitable organic solvent such as tetrahydrofuran is added an acid, preferably acetic acid, and a reducing agent such as zinc dust to yield a product in which R is hydrogen. This is subsequently reacted with a halo-R$^7$ compound, wherein R$^7$ is C$_{2-6}$alkyl or C$_{3-5}$alkenyl, to yield Formula (I) compounds wherein R is C$_{2-6}$alkyl or C$_{3-5}$alkenyl, respectively.

The substituted thiophenols and haloacetones used as starting materials in Scheme I are commercially available or can be synthesized from available materials by known methods. Additionally, the reactants used in Schemes I through III are available or can be synthesized from available materials by known methods.

The pharmaceutically acceptable, nontoxic, acid addition salts having the utility of the free bases of Formula (I) are formed with inorganic or organic acids by methods well known in the art. Representative examples of suitable acids are maleic, fumaric, benzoic, ascorbic, pamoic, succinic, bismethylenesalicylic, methanesulfonic, ethanedisulfonic, acetic, propionic, tartaric, salicylic, citric, gluconic, aspartic, stearic, palmitic, itaconic, glycolic, p-aminobenzoic, glutamic, benzenesulfonic, hydrochloric, hydrobromic, sulfuric, cyclohexylsulfamic, phosphoric and nitric acids.

Because the compounds of Formula (I) are α-adrenoceptor antagonists they are useful in treating cardiovascular diseases in which changes in vascular resistance are desirable, including hypertension, pulmonary hypertension, congestive heart failure, myocardial ischemia, angina pectoris, and peripheral vascular disease. Formula (I) compounds also are useful in treating benign prostatic hypertrophy, diabetes, glaucoma, ocular hypertension, obesity, disorders of gastrointestinal motility, including colonic spasm, irritable bowel syndrome, and constipation, impotence, and central nervous system disorders such as depression and senile dementia. Additionally, the invented compounds are useful in treating diseases resulting from inappropriate platelet aggregation.

The α-adrenoceptor activity of certain compounds of the present invention was determined using the following in vitro systems.

Alpha$_1$ adrenoceptor antagonist activity was determined using the rabbit aorta. Male New Zealand White rabbits (2-4 Kg) were euthanized by cervical concussion. A 4 cm portion of the thoracic aorta was removed and placed in a dish of cold (10° C.) Krebs-Hensleit solution. The tissue was cleaned of fat and connective tissue and cut into segments of approximately 3 mm in length. These segments were suspended in 10 ml tissue baths via hangers constructed of 0.25 mm tungsten wire. One hanger was fixed to a support in the bath and the other was attached via silk thread to a force-displacement transducer.

Tissue segments were equilibrated for 2 hours prior to drug testing, during which time basal tension was maintained at 2 gm. Tissues were washed at 30 minute intervals during this equilibration period. The Krebs-Hensleit solution contained cocaine (6 μM) to block neuronal uptake and propranolol (1 μM) to block beta adrenoceptors. Tissues were usually challenged once with norepinephrine (0.1 μM) during the equilibration period to check for viability.

A cumulative concentration-response curve to norepinephrine was obtained in each aortic segment. Following washout of norepinephrine, the α-adrenoceptor antagonist to be tested was added to the bath. After the tissue had been in contact with the antagonist for 30-60 minutes, the norepinephrine concentration response-curve was repeated in the presence of antagonist. The tissue was then washed again, and a tenfold higher concentration of antagonist added. Following equilibration (30-60 minutes), a third norepinephrine concentration-response curve was determined in the presence of the antagonist.

The receptor dissociation constant ($K_B$) for the antagonist was determined using the relationship $$K_B = \frac{\text{Antagonist Concentration}}{\text{Dose Ratio} - 1}$$

(Furchgott, R. F., *Handbook of Experimental Pharmacology*, eds. Eichler, et al., pp. 283-335 (Springer 1972)). The $K_B$ value obtained at each antagonist concentration was averaged to obtain a mean $K_B$ for each experiment.

Alpha$_2$ adrenoceptor antagonist activity of the compounds was determined using the isolated, superfused guinea pig left atrium. Briefly, the heart is removed from a pentobarbital-anesthetized male guinea pig. The left atrium is separated, dissected free of extraneous tissue and mounted in a 2 ml superfusion chamber. The tissue is paced at 30 pulse/minute and the sympathetic nerves excited at 6 minute intervals by field stimulation. The response to nerve stimulation is measured as the difference in contractile force between the basal contraction and peak contraction following a nerve stimulation. A concentration-response curve for B-HT 920 (a known α$_2$ agonist) is prepared by administering increasing concentrations of B-HT 920 following each successive stimulation. The tissue then is superfused for thirty minutes with the α-adrenoceptor antagonist to be tested and the B-HT 920 concentration-effect curve is repeated in the presence of antagonist. Data are reported as $K_B$, defined above. Additional details of this test system are found in Hieble, J. P. and R. G. Pendleton, *Arch. Pharmacol.*, 309:217-224 (1979).

Alpha$_3$ adrenoceptor antagonist receptor activity was determined using the dog saphenous vein (DSV) as the test system. This test system has been shown a suitable preparation in which to characterize postsynaptic α$_2$ (α$_3$) adrenoceptors, Sullivan, A. T. and G. M. Drew, *Arch. Pharmacol.*, 314:249-58 (1980). This test system is prepared by removing the lateral saphenous vein from an anesthetized dog and cutting the vein into segments of 4 mm in length. Segments are mounted as described for the isolated rabbit aorta.

The α$_3$ adrenoceptor antagonist activity of the compounds of interest is determined by measuring shifts in the dose-response curve of a specific agonist induced by the tested compounds. The α$_2$, α$_3$ agonist, B-HT 920, was used in testing the compounds listed in Table I.

Representative Formula (I) compounds which were tested using the above described in vitro test systems are listed in Table 1. Each of the compounds tested was found to have activity at one or more of the α adrenoceptor subtypes. Each of the compounds listed in Table 1 are Formula (Ia) compounds in which X is chloro, R is methyl unless otherwise indicated, and R$^1$ is hydrogen unless otherwise indicated.

TABLE 1

| Y | Z |
|---|---|
| CONH$_2$ | H |
| CON(CH$_3$)$_2$ | H |
| H | H |
| CONHCH$_3$ | H |
| COOC$_2$H$_5$ | H |
| COOC$_2$H$_5$ | CH$_3$ |
| CH$_2$OH | H |
| H | H (R is H) |
| CO$_2$C$_2$H$_5$ | Ph |
| CN | Ph |
| H | H (R$^1$ is CH$_3$) |
| CH$_3$ | H |

The antihypertensive activity of certain compounds of the present invention was determined using the spontaneously hypertensive rat model. The details of this in vivo test system are found in Roesler, J. M., et al., *J. Pharmacol. Exp. Ther.*, 236:1-7 (1986).

The compound of Example 4 produced a dose related reduction in arterial blood pressure in spontaneously hypertensive rats following oral administration over the dose range of 3-20 mg/kg.

Novel pharmaceutical compositions are obtained when the compounds are incorporated with pharmaceutical carriers into convenient dosage forms such as capsules, tablets, or injectable preparations. Solid or liquid pharmaceutical carriers can be employed. Solid carriers include, starch, lactose, calcium sulfate dihydrate, terra alba, sucrose, talc, gelatin, agar, pectin, acacia, magnesium stearate, and stearic acid. Liquid carriers include syrup, peanut oil, olive oil, saline, and water. Similarly, the carrier or diluent may include any prolonged release material, such as glyceryl monostearate or glyceryl distearate, alone or with a wax. The amount of solid carrier varies widely but, preferably, will be from about 25 mg to about 1 g per dosage unit. When a liquid carrier is used, the preparation will be in the form of a syrup, elixir, emulsion, soft gelatin capsule, sterile injectable liquid, or an aqueous or nonaqueous liquid suspension or solution.

The pharmaceutical preparations are made following conventional techniques of a pharmaceutical chemist involving mixing, granulating and compressing, when necessary, for tablet forms, or mixing, filling, and dissolving the ingredients, as appropriate, to give the desired oral or parenteral products.

Doses of the present compounds in a pharmaceutical dosage unit will be an efficacious, nontoxic quantity selected from the range of 0.01–100 mg/kg of active compound, preferably 0.1–50 mg/kg. The selected dose is administered to a human patient in need of treatment from 1–6 times daily, orally, rectally, topically, by inhalation, or injection, or continuously by infusion. Oral administration, however, is preferred because it is more convenient for the patient.

The following examples are illustrative of preparation of Formula (I) compounds. The examples are not intended to limit the scope of the invention as defined hereinabove and as claimed below.

EXAMPLE 1

Method A—Ethyl 7-Chloro-3,4,5,6-tetrahydro-4-methylthieno[4,3,2-ef][3]benzazepine-2-carboxylate (i) 1-[(4-Chlorophenyl)thio]-2-propanone Chloroacetone (32.3 g, 0.347 mol) was added to a mixture of 4-chlorothiophenol (50 g, 0.347 mol) and sodium hydroxide (14 g, 0.347 mol) in water (400 ml) and the mixture was stirred at 25° C. for 1 hour. The mixture was extracted with ethyl ether and the organic phase was washed with water, dried with magnesium sulfate and concentrated to give 68 g (98%) of 1-[(4-chlorophenyl)thio]-2-propanone.

(ii) 5-Chloro-3-methylbenzo[b]thiophene

1-[(4-Chlorophenyl)thio]-2-propanone (50 g, 0.25 mol) was added to polyphosphoric acid (300 g) and the mixture was stirred as the temperature was gradually raised to 120° C. as an exotherm started. The mixture was stirred at 130° C. for 1 hour, diluted with water, extracted with ethyl ether and the organic phase was dried and concentrated. The residue was stirred in methanol (200 ml), filtered and the filtrate concentrated to give 17.5 g (40%) of 5-chloro-3-methylbenzo[b]thiophene: bp 120° C. (0.6 mm).

(iii) Ethyl 5-Chloro-3-methylbenzo[b]thiophene-2-carboxylate

Butyllithium in hexane (2.6M, 2.3 ml) was added to a solution of 5-chloro-3-methylbenzo[b]thiophene (1.0 g, 6 mmol) in ethyl ether (20 ml) stirred at 0° C. under argon. The mixture was stirred for 30 minutes and transferred slowly under argon pressure to a stirred solution of ethyl chloroformate (0.63 g, 6 mmol) in ethyl ether (20 ml). The mixture was stirred at 0° C. for 30 minutes and at 25° C. for 1.5 hours. The mixture was treated with water and the organic phase was dried, concentrated and triturated with hexane to give 1.0 g (67%) of ethyl 5-chloro-3-methylbenzo[b]thiophene-2-carboxylate: mp 92.5°–94° C.

(iv) Ethyl 3-Bromomethyl-5-chlorobenzo[b]thiophene-2-carboxylate

A mixture of ethyl 5-chloro-3-methylbenzo[b]thiophene-2-carboxylate (9.0 g, 0.035 mol), N-bromosuccinimide (6.53 g, 0.037 mol) and benzoyl peroxide (130 mg) in carbon tetrachloride (150 ml) was refluxed and illuminated with a sunlamp for 2 hours. The resulting suspension was cooled, filtered and the filter cake was triturated with methanol to give 9.9 g (85%) of the methanol-insoluble ethyl 3-bromomethyl-5-chlorobenzo[b]thiophene-2-carboxylate: mp 148°–150° C.

(v) Ethyl 5-Chloro-3-[N-(2,2-dimethoxyethyl)-N-methyl(aminomethyl)]benzo[b]thiophene-2-carboxylate A mixture of ethyl 3-bromomethyl-5-chlorobenzo[b]thiophene-2-carboxylate (11.0 g, 0.033 mol), methylaminoacetaldehyde dimethyl acetal (4.76 g, 0.04 mol) and potassium carbonate (11.4 g, 0.8 mol) in dry acetone (200 ml) was stirred for 48 hours, filtered and the filtrate concentrated to give 11.8 g (96%) of ethyl 5-chloro-3-[N-(2,2-dimethoxyethyl)-N-methyl-(aminomethyl)]benzo[b]thiophene-2-carboxylate.

(vi) Ethyl 7-Chloro-3,4-dihydro-4-methylthieno[4,3,2-ef][3]benzazepine-2-carboxylate Ethyl 5-chloro-3-[N-(2,2-dimethoxyethyl)-N-methyl-(aminomethyl)]benzo[b]thiophene-2-carboxylate (3.0 g, 8.1 mmol) was added in portions to trifluoromethanesulfonic acid (10 ml) stirred at 0° C. under argon. The mixture was stirred at 25° C. for 45 minutes and diluted with water. The mixture was basified with aqueous sodium hydroxide and extracted with ethyl ether to give ethyl 7-chloro-3,4-dihydro-4-methylthieno-[4,3,2-ef][3]benzazepine-2-carboxylate.

(vii) Ethyl 7-Chloro-3,4,5,6-tetrahydro-4-methylthieno[4,3,2-ef][3]benzazepine-2-carboxylate Diborane in tetrahydrofuran (1M, 40 ml) was added to a solution of ethyl 7-chloro-3,4-dihydro-4-methylthieno[4,3,2-ef][3]benzazepine-2-carboxylate (2.8 g) in tetrahydrofuran (30 ml) stirred at 0° C. The mixture was refluxed for 3 hours and stirred at 25° C. for 16 hours, cooled, treated with methanol (50 ml), refluxed for 18 hours and concentrated. The residue was triturated with ethyl ether-hexane (3:1) to give 1.6 g (64%) of ethyl 7-chloro-3,4,5,6-tetrahydro-4-methylthieno[4,3,2-ef][3]benzazepine-2-carboxylate: mp 138°–140° C. The free base was treated with hydrogen chloride to give ethyl 7-chloro-3,4,5,6-tetrahydro-4-methylthieno[4,3,2-ef][3]benzazepine-2-carboxylate hydrochloride: mp 240° C.

Method B—Methyl 7-Chloro-3,4,5,6-tetrahydro-4-methylthieno[4,3,2-ef][3]benzazepine-2-carboxylate (i) 3-Bromomethyl-5-chlorobenzo[b]thiophene Using the general procedure of Example 1, Method A, (iv), replacing ethyl 5-chloro-3-methylbenzo[b]thiophene-2-carboxylate with 5-chloro-3-methylbenzo[b]thiophene gave 2.78 g (57%) of 3-bromomethyl-5-chlorobenzo[b]thiophene: mp 126°–128° C.

(ii) 5-Chloro-3-[N-(2,2-dimethoxyethyl)-N-methyl-(aminomethyl)]benzo[b]thiophene Using the general procedure of Example 1, Method A, (v), replacing ethyl 3-bromomethyl-5-chlorobenzo[b]thiophene-2-carboxylate with 3-bromomethyl-5-chlorobenzo[b]thiophene gave 2.1 g (95%) of 5-chloro-3-[N-(2,2-dimethoxyethyl)-N-methyl-(aminomethyl)-]benzo[b]thiophene.

(iii) 5-Chloro-3-[N-(2,2-dimethoxyethyl)-N-methyl-(aminomethyl)]benzo[b]thiophene-2-carboxylic Acid Butyllithium in tetrahydrofuran (2.6M, 0.04 mol) was added slowly to a solution of 5-chloro-3-[N-(2,2-dimethoxyethyl)-N-methyl(aminomethyl)]benzo[b]thiophene (10 g, 0.033 mol) in freshly distilled tetrahydrofuran (100 ml) stirred at −30° C. under argon. The mixture was stirred for 30 minutes, treated with dry carbon dioxide for 5 minutes and allowed to warm to 25° C. The mixture was treated with methanol, poured into ice water and extracted with ethyl ether. The aqueous phase was adjusted to pH 7.5 and extracted with methylene chloride. The organic phase was washed with water, dried with magnesium sulfate and concentrated to give 6.0 g (54%) of 5-chloro-3-[N-(2,2-dimethoxyethyl)-

N-methyl(aminomethyl)]benzo[b]thiophene-2-carboxylic acid.

(iv) Methyl 5-Chloro-3-[N-(2,2-dimethoxyethyl)-N-methyl(aminomethyl)]benzo[b]thiophene-2-carboxylate A suspension of 5-chloro-3-[N-(2,2-dimethoxyethyl)-N-methyl(aminomethyl)]benzo[b]thiophene-2-carboxylic acid (5.0 g, 14.5 mmol) in methylene chloride-tetrahydrofuran was stirred at 0° C. and treated with excess diazomethane in ethyl ether. The mixture was stirred for 2 hours at 0° C., treated with a stream of argon and concentrated to give 5.0 g (96%) of methyl 5-chloro-3-[N-(2,2-dimethoxyethyl)-N-methyl-(aminomethyl)]benzo[b]thiophene-2-carboxylate.

(v) Methyl 7-Chloro-3,4-dihydro-4-methylthieno-[4,3,2-ef][3]benzazepine-2-carboxylate Using the general procedure of Example 1, Method A, (vi), replacing ethyl 5-chloro-3-[N-(2,2-dimethoxyethyl)-N-methyl(aminomethyl)]benzo[b]thiophene-2-carboxylate with methyl 5-chloro-3-[N-(2,2-dimethoxyethyl)-N-methyl(aminomethyl)]benzo[b]thiophene-2-carboxylate gave methyl 7-chloro-3,4-dihydro-4-methylthieno[4,3,2-ef][3]benzazepine-2-carboxylate.

(vi) Methyl 7-Chloro-3,4,5,6-tetrahydro-4-methylthieno[4,3,2-ef][3]benzazepine-2-carboxylate A solution of methyl 7-chloro-3,4-dihydro-4-methylthieno[4,3,2-ef][3]benzazepine-2-carboxylate in ethanol (30 ml) containing platinum oxide (0.3 g) was shaken under hydrogen (30 psi) for 2 hours. The mixture was filtered, concentrated and treated with ethereal hydrogen chloride to give methyl 7-chloro-3,4,5,6-tetrahydro-4-methylthieno[4,3,2-ef][3]benzazepine-2-carboxylate hydrochloride: mp 215°–216° C.

EXAMPLE 2

7-Chloro-3,4,5,6-tetrahydro-4-methylthieno-[4,3,2-ef][3]benzazepine-2-methanol

A solution of methyl 7-chloro-3,4,5,6-tetrahydro-4-methylthieno[4,3,2-ef][3]benzazepine-2-carboxylate (4.0 g, 13.5 mmol), prepared as in Example 1, in ethyl ether (48 ml) was treated with lithium aluminum hydride (0.53 g, 14 mmol). The mixture was stirred for 1.5 hours, cooled and treated carefully with water (2.0 ml), 10% sodium hydroxide (1.0 ml) and water (2.0 ml). The resulting mixture was filtered and the solvent evaporated to give 2.1 g (57%) of 7-chloro-3,4,5,6-tetrahydro-4-methylthieno[4,3,2-ef][3]benzazepine-2-methanol: mp 184°–185° C.

EXAMPLE 3

7-Chloro-3,4,5,6-tetrahydro-4-methylthieno-[4,3,2-ef][3]benzazepine-2-carboxaldehyde A solution of 7-chloro-3,4,5,6-tetrahydro-4-methylthieno[4,3,2-ef][3]benzazepine-2-methanol, prepared as in Example 2, (1.6 g, 6 mmol) in dichloromethane (150 ml) was stirred under argon with activated manganese dioxide (8.3 g) for 2 hours. The mixture was filtered through an acid washed silicon dioxide filtration agent (Celite®) and the filtrate was dried with magnesium sulfate and concentrated to give a 63% yield of 7-chloro-3,4,5,6-tetrahydro-4-methylthieno[4,3,2-ef][3]benzazepine-2-carboxaldehyde.

EXAMPLE 4

7-Chloro-2-ethenyl-3,4,5,6-tetrahydro-4-methyl-thieno[4,3,2-ef][3]benzazepine

Sodium hydride (60% dispersion in mineral oil, 3.8 mmol) was added to a stirred solution of methyltriphenylphosphonium bromide (1.35 g, 3.8 mmol) in dry tetrahydrofuran (30 ml) and stirred for 15 minutes. The mixture was treated with a solution of 7-chloro-3,4,5,6-tetrahydro-4-methylthieno[4,3,2-ef][3]benzazepine-2-carboxaldehyde, prepared as in Example 3, (0.5 g, 1.9 mmol) in dimethylformamide (4 ml), stirred at 25° C. for 16 hours, quenched with ice and extracted with ethyl acetate. The organic phase was washed, dried and concentrated and the residue was chromatographed on silica gel eluted with a gradient of methylene chloride to methanol-methylene chloride (3.5:96.5). The product was treated with hydrogen chloride to give 0.2 g (35%) of 7-chloro-2-ethenyl-3,4,5,6-tetrahydro-4-methyl-thieno[4,3,2-ef][3]benzazepine hydrochloride: mp 234°–236° C.

EXAMPLE 5

7-Chloro-3,4,5,6-tetrahydro-4-methyl-2-(2-methyl-1-propenyl)thieno[4,3,2-ef][3]benzazepine A solution of butyllithium in hexane (2.6m, 1.3 ml, 3.4 mmol) is added to a suspension of isopropyltriphenylphosphonium iodide (1.5 g, 3.4 mmol) in freshly distilled tetrahydrofuran (20 ml) stirred under argon at −15° C. The mixture is stirred at −10° C. to −15° C. for 20 minutes and treated with a solution of 7-chloro-3,4,5,6-tetrahydro-4-methylthieno[4,3,2-ef][3]benzazepine-2-carboxaldehyde, prepared as in Example 3, (3.2 mmol) in tetrahydrofuran (15 ml) added dropwise over 10 minutes. The reaction is stirred for 2 hours, quenched with ethanol (3 ml) and the solvents evaporated. The residue is triturated with ethyl ether and the organic extract is treated with hydrogen chloride to give 7-chloro-3,4,5,6-tetrahydro-4-methyl-2-(2-methyl-1-propenyl)thieno[4,3,2-ef][3]benzazepine hydrochloride.

EXAMPLE 6

Ethyl (E)-3-(7-Chloro-3,4,5,6-tetrahydro-4-methyl-thieno[4,3,2-ef][3]benzazepin-2-yl)-2-propenoate Sodium hydride (50% dispersion in mineral oil, 58 mg, 1.2 mmol) was added to a stirred solution of triethyl phosphonoacetate (268 mg, 1.2 mmol) in ethyl ether (30 ml) and stirred for 15 minutes. The mixture was treated with a solution of 7-chloro-3,4,5,6-tetrahydro-4-methyl-thieno[4,3,2-ef][3]benzazepine-2-carboxaldehyde, prepared as in Example 3, (300 mg, 1.4 mmol) in ethyl ether (30 ml), stirred at 25° C. for 16 hours, quenched with water and extracted with ethyl ether. The organic phase was washed, dried and concentrated and the residue treated with ethereal hydrogen chloride to give 230 mg (40%) of ethyl (E)-3-(7-chloro-3,4,5,6-tetrahydro-4-methylthieno[4,3,2-ef][3]benzazepine-2-yl)-2-propenoate hydrochloride: mp 234°–236° C.

EXAMPLE 7

Ethyl (E)-3-(7-Chloro-3,4,5,6-tetrahydrothieno[4,3,2-ef][3]benzazepin-2-yl)-2-propenoate A solution of ethyl (E)-3-(7-chloro-3,4,5,6-tetrahydro-4-methylthieno[4,3,2-ef][3]benzazepin-2-yl)-2-propenoate, prepared as in Example 6, (5.9 mmol) in 1,2-dichloroethane (75 ml) is treated with 2,2,2-trichloroethyl chloroformate (3.75 g, 17.7 mmol). The resulting suspension is refluxed for 7 hours and the solvent is evaporated.

A solution of the trichloroethyl carbamate (4.16 mmol) in tetrahydrofuran (70 ml) and glacial acetic acid (10 ml) is treated with activated zinc powder (5.0 g) and the resulting suspension is stirred at room temperature for 1 hour. The mixture is filtered, concentrated, and the residue is partitioned between 5% sodium bicarbonate and dichloromethane. The organic phase is dried with magnesium sulfate and evaporated. The residue is dissolved in ethyl ether and treated with hydrogen chloride to give ethyl (E)-3-(7-chloro-3,4,5,6-tetrahydrothieno[4,3,2-ef][3]benzazepin-2-yl)-2-propenoate hydrochloride.

EXAMPLE 8

Ethyl (E)-3-[7-Chloro-3,4,5,6-tetrahydro-4-(2-propenyl)-thieno[4,3,2-ef][3]benzazepin-2-yl]-2-propenoate A solution of ethyl (E)-3-(7-chloro-3,4,5,6-tetrahydrothieno[4,3,2-ef][3]benzazepin-2-yl)-2-propenoate (0.56 mmol), prepared as in Example 7, in dry acetone (30 ml) is stirred and treated with potassium carbonate (0.5 g) and allyl iodide (0.10 g, 0.58 mmol). The reaction is stirred for 16 hours, filtered, evaporated, and the residue is partitioned between ethyl ether and water. The organic phase is dried with magnesium sulfate and treated with hydrogen chloride to give ethyl (E)-3-[7-chloro-3,4,5,6-tetrahydro-4-(2-propenyl)thieno[4,3,2-ef][3]benzazepin-2-yl]-2-propenoate.

EXAMPLE 9

Ethyl (E)-3-(7-Chloro-3,4,5,6-tetrahydro-4-methylthieno[4,3,2-ef][3]benzazepin-2-yl)-2-methyl-2-propenoate Using the general procedure of Example 6, replacing triethyl phosphonoacetate with triethyl 2-phosphonopropanoate gave ethyl (E)-3-(7-chloro-3,4,5,6-tetrahydro-4-methylthieno[4,3,2-ef][3]benzazepin-2-yl)-2-methyl-2-propenoate hydrochloride: mp 200° C. (dec).

EXAMPLE 10

Ethyl (E)-3-(7-Chloro-3,4,5,6-tetrahydro-4-methylthieno[4,3,2-ef][3]benzazepin-2-yl)-2-propyl-2-propenoate Using the general procedure of Example 6, replacing triethyl phosphonoacetate with triethyl 2-phosphonopentanoate gives ethyl (E)-3-(7-chloro-3,4,5,6-tetrahydro-4-methylthieno[4,3,2-ef][3]benzazepin-2-yl)-2-propyl-2-propenoate hydrochloride.

EXAMPLE 11

Ethyl (Z)-3-(7-Chloro-3,4,5,6-tetrahydro-4-methylthieno[4,3,2-ef][3]benzazepin-2-yl)-2-fluoro-2-propenoate A solution of diethylaluminum chloride in hexane (1m, 4.4 mmol, 4.4 ml) is added to a stirred suspension of copper (I) bromide (58 mg, 0.2 mmol) and activated zinc dust (0.4 g, 6 mmol) in freshly distilled tetrahydrofuran (35 ml). The mixture is cooled to −30° C., stirred vigorously, and treated with a solution of 7-chloro-3,4,5,6-tetrahydro-4-methylthieno[4,3,2-ef][3]benzazepine-2-carboxaldehyde (4.0 mmol), prepared as in Example 3, and ethyl bromofluoroacetate (0.74 g, 4.0 mmol) in tetrahydrofuran (15 ml) is added dropwise over 30 minutes. The reaction temperature is allowed to rise slowly to 0° C. over a period of 40 minutes. The resulting suspension then is warmed to room temperature and stirred for 1.5 hours. Ethyl ether is added to bring the total volume to 250 ml and the mixture is treated with water (10 ml) and 5% sodium bicarbonate (15 ml). The mixture is filtered and the organic phase is washed with water and brine, dried with magnesium sulfate and evaporated to give a mixture of isomers of ethyl 3-(7-chloro-3,4,5,6-tetrahydro-4-methylthieno[4,3,2-ef][3]benzazepin-2-yl)-2-fluoro-3-hydroxypropanoate.

A solution of ethyl 3-(7-chloro-3,4,5,6-tetrahydro-4-methylthieno[4,3,2-ef][3]benzazepin-2-yl)-2-fluoro-3-hydroxypropanoate (1.8 mmol) and triethylamine (3 ml) in dry dichloromethane (35 ml) is stirred at −20° C. and a solution of methanesulfonyl chloride (0.21 g, 1.9 mmol) in methylene chloride (5 ml) is added dropwise over a period of 2–3 minutes. The reaction is stirred at −20° C. for 20 minutes, and then at room temperature for 2 hours. The mixture is treated with 5% sodium bicarbonate (5 ml) and the organic phase is dried with magnesium sulfate and evaporated to give ethyl (Z)-3-(7-chloro-3,4,5,6-tetrahydro-4-methylthieno[4,3,2-ef][3]benzazepin-2-yl)-2-fluoro-2-propenoate.

EXAMPLE 12

Ethyl (E)-2-Chloro-3-(7-chloro-3,4,5,6-tetrahydro-4-methylthieno[4,3,2-ef][3]benzazepin-2-yl)-2-propenoate and Ethyl (Z)-2-Chloro-3-(7-chloro-3,4,5,6-tetrahydro-4-methylthieno[4,3,2-ef][3]benzazepin-2-yl)-2-propenoate A 50% dispersion of sodium hydride in mineral oil (92 mg, 1.9 mmol) is washed under argon with hexane and suspended in dry 1,2-dimethoxyethane (1 ml). The suspension is stirred under argon, cooled to 10° C., and treated with a solution of triethyl phosphono-2-chloroacetate (450 mg, 1.7 mmol) in dry 1,2-dimethoxyethane (2 ml). The mixture is warmed to 20° C., treated with a solution of 7-chloro-3,4,5,6-tetrahydro-4-methylthieno[4,3,2-ef][3]benzazepine-2-carboxaldehyde (1.7 mmol), prepared as in Example 3, in 1,2-dimethoxyethane (4 ml) and stirred for 2.5 hours. The reaction is poured into ice and the mixture is extracted with dichloromethane. The organic phase is dried with magnesium sulfate and evaporated. The residue is chromatographed on silica eluting with methanol in chloroform to give two fractions. The individual fractions are further purified by reverse phase thin layer chromatography on C-18 silica eluting with water in methanol to give the pure E and Z isomers. These are separately dissolved in methanol and treated with ethereal hydrogen chloride to give ethyl (E)-2-chloro-3-(7-chloro-3,4,5,6-tetrahydro-4-methylthieno[4,3,2-ef][3]benzazepin-2-yl)-2-propenoate hydrochloride and ethyl (Z)-2-chloro-3-(7-chloro-3,4,5,6-tetrahydro-4-methylthieno[4,3,2-ef][3]benzazepin-2-yl)-2-propenoate hydrochloride.

EXAMPLE 13

Ethyl (Z)-2-Bromo-3-(7-chloro-3,4,5,6-tetrahydro-4-methylthieno[4,3,2-ef][3]benzazepin-2-yl)-2-propenoate A 50% suspension of sodium hydride in mineral oil (0.1 g, 2 mmol) is washed under argon with hexane and suspended in dry 2-ethoxyethyl ether (2 ml). The suspension is stirred under argon, treated dropwise with a solution of triethyl phosphonoacetate (450 mg, 2 mmol), and stirred until hydrogen evolution ceased. The resulting mixture is treated with bromine (320 mg, 2 mmol) added dropwise at a rate to keep the internal temperature below 25° C. The mixture is warmed to 40° C. for a brief period, cooled to 10° C., treated with sodium hydride (0.1 g, 2 mmol), and stirred until hydrogen evolution ceased and the internal temperature reached 20° C. The resulting mixture is stirred and treated with a solution of 7-chloro-3,4,5,6-tetrahydro-4-methylthieno[4,3,2-ef][3]benzazepine-2-carboxaldehyde (2.0 mmol), prepared as in Example 3, in 2-ethoxyethyl ether (4 ml) added dropwise at a rate to keep the internal temperature below 30° C. The reaction is stirred for 2 hours, treated with water (60 ml) and extracted with ethyl ether. The organic phase is dried with magnesium sulfate, evaporated and treated with hydrogen chloride to give (Z)-2-bromo-3-(7-chloro-3,4,5,6-tetrahydro-4-methylthieno[4,3,2-ef][3]benzazepin-2-yl)-2-propenoate.

EXAMPLE 14

(E)-3-(7-Chloro-3,4,5,6-tetrahydro-4-methylthieno[4,3,2-ef][3]benzazepin-2-yl)-2-propenoic Acid Ethyl (E)-3-(7-chloro-3,4,5,6-tetrahydro-4-methylthieno[4,3,2-ef][3]benzazepin-2-yl)-2-propenoate (0.5 g, 1.5 mmol), prepared as in Example 6, was suspended in 6N hydrochloric acid (6 ml) and acetic acid (10 ml) and the mixture was stirred at 50° C. for 45 minutes, cooled and concentrated to give 0.6 g of (E)-3-(7-chloro-3,4,5,6-tetrahydro-4-methylthieno[4,3,2-ef][3]benzazepin-2-yl)-2-propenoic acid hydrochloride.

EXAMPLE 15

Methyl (E)-3-(7-Chloro-3,4,5,6-tetrahydro-4-methylthieno[4,3,2-ef][3]benzazepin-2-yl)-2-propenoate Using the general procedure of Example 6, replacing triethyl phosphonoacetate with methyl diethylphosphonoacetate gives methyl (E)-3-(7-chloro-3,4,5,6-tetrahydro-4-methylthieno[4,3,2-ef][3]benzazepin-2-yl)-2-propenoate hydrochloride.

EXAMPLE 16

(E)-3-(7-Chloro-3,4,5,6-tetrahydro-4-methylthieno[4,3,2-ef][3]benzazepin-2-yl)-2-propenamide (E)-3-(7-Chloro-3,4,5,6-tetrahydro-4-methylthieno[4,3,2-ef][3]benzazepin-2-yl)-2-propenoic acid (0.1 g, 0.3 mmol), prepared as in Example 14, and thionyl chloride (2 ml) were mixed, stirred under argon, and refluxed for 45 minutes. The thionyl chloride was evaporated to give (E)-3-(7-chloro-3,4,5,6-tetrahydro-4-methylthieno[4,3,2-ef][3]benzazepin-2-yl)-2-propenoyl chloride hydrochloride.

The propenoyl chloride was suspended in tetrahydrofuran (50 ml), stirred, cooled to −78° C., and treated with a stream of ammonia for 5 minutes. The mixture was allowed to warm to room temperature and stirred for 0.5 hours. The mixture was filtered and the filtrate was concentrated and treated with hydrogen chloride to give (E)-3-(7-chloro-3,4,5,6-tetrahydro-4-methylthieno[4,3,2-ef][3]benzazepin-2-yl)-2-propenamide hydrochloride: mp 276° C. (dec).

EXAMPLE 17

(E)-3-(7-Chloro-3,4,5,6-tetrahydro-4-methylthieno[4,3,2-ef][3]benzazepin-2-yl)-N-methyl-2-propenamide Using the general procedure of Example 16, replacing ammonia with methylamine gave (E)-3-(7-chloro-3,4,5,6-tetrahydro-4-methylthieno[4,3,2-ef][3]benzazepin-2-yl)-N-methyl-2-propenamide: mp 185° C. (dec).

EXAMPLE 18

(E)-3-(7-Chloro-3,4,5,6-tetrahydro-4-methylthieno[4,3,2-ef][3]benzazepin-2-yl)-N,N-dimethyl-2-propenamide Using the procedure of Example 16, replacing ammonia with dimethylamine gave (E)-3-(7-chloro-3,4,5,6-tetrahydro-4-methylthieno[4,3,2-ef][3]benzazepin-2-yl)-N,N-dimethyl-2-propenamide hydrochloride: mp 278° C.

EXAMPLE 19

(E)-3-(7-Chloro-3,4,5,6-tetrahydro-4-methylthieno[4,3,2-ef][3]benzazepin-2-yl)-N,2-dimethyl-2-propenamide (i) (E)-3-(7-Chloro-3,4,5,6-tetrahydro-4-methylthieno[4,3,2-ef][3]benzazepin-2-yl)-2-methyl-2-propenoic acid Using the general procedure of Example /4, replacing ethyl (E)-3-(7-chloro-3,4,5,6-tetrahydro-4-methylthieno[4,3,2-ef][3]benzazepin-2-yl)-2-propenoate with ethyl (E)-3-(7-chloro-3,4,5,6-tetrahydro-4-methylthieno[4,3,2-e,f][3]benzazepin-2-yl)-2-methyl-2-propenoate, prepared as in Example 9, gives (E)-3-(7-chloro-3,4,5,6-tetrahydro-4-methylthieno[4,3,2-ef][3]benzazepin-2-yl)-2-methyl-2-propenoic acid hydrochloride.

(ii) (E)-3-(7-Chloro-3,4,5,6-tetrahydro-4-methylthieno[4,3,2-ef][3]benzazepin-2-yl)-N,2-dimethyl-2-propenamide Using the general procedure of Example 16, replacing (E)-3-(7-chloro-3,4,5,6-tetrahydro-4-methylthieno[4,3,2-ef][3]benzazepin-2-yl)-2-propenoic acid with (E)-3-(7-chloro-3,4,5,6-tetrahydro-4-methylthieno[4,3,2-ef][3]benzazepin-2-yl)-2-methyl-2-propenoic acid and ammonia with methylamine gives (E)-3-(7-chloro-3,4,5,6-tetrahydro-4-methylthieno[4,3,2-ef][3]benzazepin-2-yl)-N,2-dimethyl-2-propenamide hydrochloride.

EXAMPLE 20

(E)-3-(7-Chloro-3,4,5,6-tetrahydro-4-methylthieno[4,3,2-ef][3]benzazepin-2-yl)-2-propenenitrile Using the general procedure of Example 6, replacing triethyl phosphonoacetate with diethyl cyanomethylphosphonate gives (E)-3-(7-chloro-3,4,5,6-tetrahydro-4-methylthieno[4,3,2-ef][3]benzazepin-2-yl)-2-propenenitrile hydrochloride.

EXAMPLE 21

(E)-4-(7-Chloro-3,4,5,6-tetrahydro-4-methylthieno[4,3,2-ef][3]benzazepin-2-yl)-3-buten-2-one A solution of 7-chloro-3,4,5,6-tetrahydro-4-methylthieno[4,3,2-ef][3]benzazepine-2-carboxaldehyde (1.3 mmol), prepared as in Example 3, in absolute ethanol (20 ml) is stirred under argon and treated with a solution of 1-triphenylphosphoranylidene-2-propanone (300 mg, 1.2 mmol) in absolute ethanol (10 ml). The reaction is stirred for 17 hours, evaporated, and the residue is dissolved in methanol and treated with ethereal hydrogen chloride to give (E)-4-(7-chloro-3,4,5,6-tetrahydro-4-methylthieno[4,3,2-ef][3]benzazepin-2-yl)-3-buten-2-one hydrochloride.

EXAMPLE 22

(E)-7-Chloro-3,4,5,6-tetrahydro-4-methyl-2-[2-(methylsulfonyl)ethenyl]thieno[4,3,2-ef][3]benzazepine Using the general procedure of Example 6, replacing triethyl phosphonacetate with dimethyl methylsulfonylmethylphosphonate gives (E)-7-chloro-3,4,5,6-tetrahydro-4-methyl-2-[2-(methylsulfonyl)ethenyl]-thieno[4,3,2-ef][3]benzazepine.

EXAMPLE 23

(E)-2-(7-Chloro-3,4,5,6-tetrahydro-4-methyl-thieno[4,3,2-ef][3]benzazepin-2-yl)-N,N-dimethyl-ethenesulfonamide A solution of 7-chloro-3,4,5,6-tetrahydro-4-methyl-thieno[4,3,2-ef][3]benzazepine-2-carboxaldehyde (1.3 mmol), prepared as in Example 3, and diethyl [[dimethyl(amino)sulfonyl]methyl]phosphonate (382 mg, 1.5 mmol) in dry methanol (10 ml) is stirred under argon and treated with methanolic sodium methoxide prepared by dissolving sodium (30 mg, 1.3 mmol) in methanol (0.75 ml). The reaction is stirred for 5 hours and treated dropwise with water (10 ml) to give (E)-2-(7-chloro-3,4,5,6-tetrahydro-4-methylthieno[4,3,2-ef][3]benzazepin-2-yl)-N,N-dimethylethenesulfonamide.

EXAMPLE 24

Diethyl (E)-[2-(7-Chloro-3,4,5,6-tetrahydro-4-methyl-thieno[4,3,2-ef][3]benzazepin-2-yl)ethenyl]phosphonate Using the general procedure of Example 6, replacing triethyl phosphonoacetate with tetraethylmethylenebisphosphonate gives diethyl (E)-[2-(7-chloro-3,4,5,6-tetrahydro-4-methylthieno[4,3,2-ef][3]benzazepin-2-yl)ethenyl]phosphonate hydrochloride.

EXAMPLE 25

7,9-Dichloro-2-ethenyl-3,4,5,6-tetrahydro-4-methyl-thieno[4,3,2-ef][3]benzazepine Using the general procedure of Example 1, replacing 4-chlorothiophenol with 2,4-dichlorothiophenol yields ethyl 7,9-dichloro-3,4,5,6-tetrahydro-4-methyl-thieno[4,3,2-ef][3]benzazepine-2-carboxylate.

Using the general procedure of Example 2, replacing ethyl 7-chloro-3,4,5,6-tetrahydro-4-methylthieno[4,3,2-ef][3]benzazepine-2-carboxylate with ethyl 7,9-dichloro-3,4,5,6-tetrahydro-4-methylthieno[4,3,2-ef][3]benzazepine-2-carboxylate yields 7,9-dichloro-3,4,5,6-tetrahydro-4-methylthieno[4,3,2-ef][3]benzazepine-2-methanol.

Using the general procedure of Example 3, replacing 7-chloro-3,4,5,6-tetrahydro-4-methylthieno[4,3,2-ef][3]benzazepine-2-methanol with 7,9-dichloro-3,4,5,6-tetrahydro-4-methylthieno[4,3,2-ef][3]benzazepine-2-methanol yields 7,9-dichloro-3,4,5,6-tetrahydro-4-methylthieno[4,3,2-ef][3]benzazepine-2-carboxaldehyde.

Using the general procedure of Example 4, replacing 7-chloro-3,4,5,6-tetrahydro-4-methylthieno[4,3,2-ef][3]benzazepine-2-carboxaldehyde with 7,9-dichloro-3,4,5,6-tetrahydro-4-methylthieno[4,3,2-ef][3]benzazepine-2-carboxaldehyde yields 7,9-dichloro-2-ethenyl-3,4,5,6-tetrahydro-4-methylthieno[4,3,2-ef][3]benzazepine.

EXAMPLE 26

Ethyl (E)-3-(7-Cyano-3,4,5,6-tetrahydro-4-methyl-thieno[4,3,2-ef][3]benzazepin-2-yl)-2-propenoate Using the general procedure of Example 1, replacing 4-chlorothiophenol with 4-bromothiophenol gives ethyl 7-bromo-3,4,5,6-tetrahydro-4-methylthieno[4,3,2-ef][3]benzazepine-2-carboxylate. The bromo compound is heated with cuprous cyanide in dimethylformamide to give ethyl 7-cyano-3,4,5,6-tetrahydro-4-methyl-thieno-[4,3,2-ef][3]benzazepine-2-carboxylate.

Using the general procedures of Examples 2, 3, and 6, the cyano-carboxylate is reduced with lithium borohydride, oxidized with manganese dioxide and condensed with triethyl phosphonoacetate to give ethyl (E)-3-(7-cyano-3,4,5,6-tetrahydro-4-methylthieno[4,3,2-ef][3]benzazepin-2-yl)-2-propenoate.

EXAMPLE 27

Ethyl (E)-3-(7-Fluoro-3,4,5 6-tetrahydro-4-methylthieno[4,3,2-ef][3]benzazepin-2-yl)-2-propenoate Using the general procedure of Example 1, replacing 4-chlorothiophenol with 4-fluorothiophenol gives ethyl 7-fluoro-3,4,5,6-tetrahydro-4-methylthieno[4,3,2-ef][3]benzazepine-2-carboxylate.

Using the general procedures of Example 2, 3, and 6, ethyl 7-fluoro-3,4,5,6-tetrahydro-4-methylthieno[4,3,2-ef][3]benzazepine-2-carboxylate is reduced, oxidized, and condensed with triethyl phosphonoacetate to give ethyl (E)-3-(7-fluoro-3,4,5,6-tetrahydro-4-methyl-thieno[4,3,2-ef][3]benzazepin-2-yl)-2-propenoate.

EXAMPLE 28

Methyl (Z)-3-(7-Chloro-3,4,5,6-tetrahydro-4-methyl-thieno[4,3,2-ef][3]benzazepin-2-yl)-2-propenoate A solution of methyl bis(2,2,2-trifluoroethyl)phosphonoacetate (0.8 g, 2.5 mmol) and 18-crown-6 (0.66 g, 2.5 mmol) in dry tetrahydrofuran (35 ml) at $-78°$ C. is stirred and treated with a solution of potassium bis(trimethylsilyl)amide (0.5M, 5.0 ml, 2.5 mmol) in toluene. A solution of 7-chloro-3,4,5,6-tetrahydro-4-methyl-thieno[4,3,2-ef[3]benzazepine-2-carboxaldehyde (2.5 mmol), prepared as in Example 3, in dry tetrahydrofuran (10 ml) is added dropwise over a period of 5 minutes. The reaction is stirred for 0.5 hours, warmed to room temperature for 45 minutes, and quenched with saturated ammonium chloride (4 ml). The resulting suspension is diluted with ethyl ether (100 ml) and extracted with water (2×10 ml). The organic layer is dried over sodium sulfate and evaporated to give methyl (Z)-3-(7-chloro-3,4,5,6-tetrahydro-4-methyl-thieno[4,3,2-ef][3]benzazepin-2-yl)-2-propenoate.

EXAMPLE 29

Ethyl
(E)-3-(7-Chloro-4-ethyl-3,4,5,6-tetrahydrothieno[4,3,2-ef][3]benzazepin-2-yl)-2-propenoate (i) Ethyl 7-chloro-3,4,5,6-tetrahydrothieno[4,3,2-ef][3]benzazepine-2-carboxylate A mixture of ethyl 7-chloro-3,4,5,6-tetrahydro-4-methylthieno[4,3,2-ef][3]benzazepine-2-carboxylate, prepared as in Example 1, (4.5 g, 14.5 mmol), trichloroethyl chloroformate (12.7 g, 58 mmol) and potassium carbonate (1.0 g) in toluene (100 ml) was heated to reflux for 72 hours, cooled and filtered. The filtrate was concentrated in vacuo, let stand and filtered to give 2.1 g of ethyl 7-chloro-3,4,5,6-tetrahydro-2-(trichloroethoxycarbonyl)thieno[4,3,2-ef][3]benzazepine-2-carboxylate.

A mixture of ethyl 7-chloro-3,4,5,6-tetrahydro-2-(trichloroethoxycarbenyl)thieno[4,3,2-ef][3]benzazepine-2-carboxylate (2.1 g) and zinc powder (4.5 g) in acetic acid was stirred for 72 hours, filtered and the filtrate was diluted with water, basified with 50% aqueous sodium hydroxide and extracted with ethyl ether. The organic phase was dried with magnesium sulfate and concentrated in vacuo to give 0.84 g of ethyl 7-chloro-3,4,5,6-tetrahydrothieno[4,3,2-ef][3]benzazepine-2-carboxylate.

(ii) 7-Chloro-4-ethyl-3,4,5,6-tetrahydrothieno[4,3,2-ef][3]benzazepine-2-methanol A solution of ethyl 7-chloro-3,4,5,6-tetrahydrothieno[4,3,2-ef][3]benzazepine-2-carboxylate (2.7 mmol) and triethylamine (3 ml) in dry tetrahydrofuran (25 ml) is stirred and treated with acetyl chloride (1.0 g, 12.7 mmol) in one portion. After 20 minutes, the reaction mixture is filtered, evaporated, and concentrated to give ethyl 4-acetyl-7-chloro-3,4,5,6-tetrahydrothieno[4,3,2-ef][3]benzazepine-2-carboxylate.

A solution of ethyl 4-acetyl-7-chloro-3,4,5,6-tetrahydrothieno[4,3,2-ef][3]benzazepine-2-carboxylate (1.67 mmol) in tetrahydrofuran (25 ml) is added dropwise to a stirred suspension of lithium aluminum hydride (0.126 g, 3.3 mmol) in ethyl ether (25 ml). Standard work-up gives 7-chloro-4-ethyl-3,4,5,6-tetrahydrothieno[4,3,2-ef][3]benzazepine-2-methanol.

(iii) 7-Chloro-4-ethyl-3,4,5,6-tetrahydrothieno[4,3,2-ef][3]benzazepine-2-carboxaldehyde Using the general procedure of Example 3, replacing 7-chloro-3,4,5,6-tetrahydro-4-methylthieno[4,3,2-ef][3]benzazepine-2-methanol with 7-chloro-4-ethyl-3,4,5,6-tetrahydrothieno[4,3,2-ef][3]benzazepine-2-methanol yields 7-chloro-4-ethyl-3,4,5,6-tetrahydrothieno[4,3,2-ef][3]benzazepine-2-carboxaldehyde.

(iv) Ethyl 3-(7-Chloro-4-ethyl-3,4,5,6-tetrahydrothieno[4,3,2-ef][3]benzazepin-2-yl)-2-propenoate Using the general procedure of Example 6, replacing 7-chloro-3,4,5,6-tetrahydro-4-methylthieno[4,3,2-ef][3]benzazepine-2-carboxaldehyde with 7-chloro-4-ethyl-3,4,5,6-tetrahydrothieno[4,3,2-ef][3]benzazepine-2-carboxaldehyde yields ethyl (E)-3-(7-chloro-4-ethyl-3,4,5,6-tetrahydrothieno[4,3,2-ef][3]benzazepin-2-yl)-2-propenoate.

EXAMPLE 30

(E)-3-(7-chloro-3,4,5,6-tetrahydro-4-methylthieno[4,3,2-ef][3]benzazepin-2-yl)-N-methyl-2-(2-hydroxyethyl)-2-propenamide Using the general procedure of Example 6, replacing triethyl phosphonoacetate with triethyl 4-hydroxy-2-phosphonobutyrate gives ethyl (E)-3-(7-chloro-3,4,5,6-tetrahydro-4-methylthieno[4,3,2-ef][3]benzazepin-2-yl)-2-(2-hydroxyethyl)-2-propenoate. Using the general procedure of Example 17, replacing ethyl (E)-3-(7-chloro-3,4,5,6-tetrahydro-4-methylthieno[4,3,2-ef][3]benzazepin-2-yl)-2-propenoate with ethyl (E)-3-(7-chloro-3,4,5,6-tetrahydro-4-methylthieno[4,3,2-ef][3]benzazepin-2-yl)-2-(2-hydroxyethyl)-2-propenoate gives (E)-3-(7-chloro-3,4,5,6-tetrahydro-4-methylthieno-[4,3,2-ef][3]benzazepin-2-yl)-N-methyl-2-(2-hydroxyethyl)-2-propenamide.

EXAMPLE 31

Ethyl
(E)-3-(9-Chloro-3,4,5,6-tetrahydro-4-methylthieno[4,3,2-ef][3]benzazepin-2-yl)-2-propenoate Using the general procedure of Example 1, replacing 4-chlorothiophenol with 2-chlorothiophenol gives ethyl 9-chloro-3,4,5,6-tetrahydro-4-methylthieno[4,3,2-ef][3]benzazepine-2-carboxylate.

Using the general procedures of Examples 2, 3, and 6, ethyl 9-chloro-3,4,5,6-tetrahydro-4-methylthieno[4,3,2-ef][3]benzazepine-2-carboxylate is reduced, oxidized, and condensed with triethyl phosphonoacetate to give ethyl (E)-3-(9-chloro-3,4,5,6-tetrahydro-4-methylthieno[4,3,2-ef][3]benzazepin-2-yl)-2-propenoate.

EXAMPLE 32

(E)-3-(7-Chloro-3,4,5,6-tetrahydro-4-methylthieno[4,3,2-ef][3]benzazepin-2-yl)-2-propen-1-ol Diisobutylaluminum hydride in toluene (1.5M, 7.5 mmol) was added to a solution of ethyl (E)-3-(7-chloro-3,4,5,6-tetrahydro-4-methylthieno[4,3,2-ef][3]benzazepin-2-yl)-2-propenoate, prepared as in Example 6, (2.9 mmol) in toluene (50 ml) stirred at 0° C. under argon. The mixture was stirred for two hours at 25° C., quenched with water, and extracted with toluene. The organic phase was dried with magnesium sulfate and concentrated to give product which was treated with hydrogen chloride to give (E)-3-(7-chloro-3,4,5,6-tetrahydro-4-methylthieno[4,3,2-ef][3]benzazepin-2-yl)-2-propen-1-ol hydrochloride: mp 160°–163° C.

EXAMPLE 33

Ethyl
(E/Z)-3-(7-Chloro-3,4,5,6-tetrahydro-4-methylthieno[4,3,2-ef][3]benzazepin-2-yl)-2-phenyl-2-propenoate Using the general procedure of Example 9, replacing triethyl 2-phosphonopropanoate with triethyl 2-phosphono-2-phenylacetate gave ethyl (E/Z)-3-(7-chloro-3,4,5,6-tetrahydro-4-methylthieno[4,3,2-ef][3]benzazepin-2-yl)-2-phenyl-2-propenoate hydrochloride.

EXAMPLE 34

Ethyl
(E/Z)-3-(7-Chloro-3,4,5,6-tetrahydro-4-methylthieno[4,3,2-ef][3]benzazepin-2-yl)-2-phenyl-2-propenenitrile Sodium (0.3 g) was added to absolute ethanol (2 ml) and the resulting solution was added to a solution of 7-chloro-3,4,5,6-tetrahydro-4-methylthieno[4,3,2-ef][3]benzazepine-2-carboxaldehyde, prepared as in Example 3, (0.3 g, 2 mmol) and phenylacetonitrile (0.35 g, 3 mmol) in ethanol (70 ml) heated on a steam bath. The mixture was stirred for 15 minutes, cooled and filtered to give ethyl (E/Z)-3-(7-chloro-3,4,5,6-tetrahydro-4-methylthieno[4,3,2-ef][3]benzazepin-2-yl)-2-phenyl-2-propenenitrile: mp 38°-139° C.

EXAMPLE 35

7-Chloro-3,4,5,6-tetrahydro-4-methyl-2-(1-methylethenyl)thieno[4,3,2-ef][3]benzazepine Methylmagnesium bromide in tetrahydrofuran (3M, 15 ml, 45 mmol) was added to a solution of ethyl 7-chloro-3,4,5,6-tetrahydro-4-methylthieno[4,3,2-ef][3]benzazepine-2-carboxylate, prepared as in Example 1, (3.09 g, 10 mmol) in tetrahydrofuran (60 ml) stirred under argon. The mixture was stirred for 1 hour, treated with water and concentrated in vacuo. The residue was partitioned between water and ethyl ether. The organic phase was dried with magnesium sulfate and concentrated in vacuo to give an oil which was chromatographed on silica gel eluted with methanol-methylene chloride (1:10) to give 1 g of 7-chloro-3,4,5,6-tetrahydro-α,α,4-trimethylthieno[4,3,2-ef][3]benzazepine-2-methanol: mp 250° C.

Triethylamine (2 ml) and methanesulfonyl chloride (1.1 g, 10 mmol) were added to a solution of 7-chloro-3,4,5,6-tetrahydro-α,α,4-trimethylthieno[4,3,2-ef][3]benzazepine-2-methanol (0.7 g, 2.3 mmol) in methylene chloride (50 ml) stirred at 0° C. The mixture was stirred for 3 hours, diluted with water, basified with 10% aqueous sodium hydroxide and extracted with ethyl ether. The organic phase was dried with magnesium sulfate and concentrated in vacuo to give an oil. The oil was dissolved in ethyl ether and treated with hydrogen chloride to give 7-chloro-3,4,5,6-tetrahydro-4-methyl-2-(1-methylethenyl)thieno[4,3,2-ef][3]benzazepine hydrochloride: mp 203°-205° C. (d).

EXAMPLE 36

(E/Z)-7-Chloro-3,4,5,6-tetrahydro-4-methyl-2-(1-propenyl)thieno[4,3,2-ef][3]benzazepine Using the general procedure of Example 4, replacing methyltriphenylphosphonium bromide with ethyltriphenylphosphonium bromide, gave (E/Z)-7-chloro-3,4,5,6-tetrahydro-4-methyl-2-(1-propenyl)thieno[4,3,2-ef][3]benzazepine hydrochloride: mp 245° C.

EXAMPLE 37

7-Chloro-2-ethenyl-3,4,5,6-tetrahydrothieno[4,3,2-ef][3]benzazepine

Using the general procedure of Example 2, replacing ethyl 7-chloro-3,4,5,6-tetrahydro-4-methylthieno[4,3,2-ef][3]benzazepine-2-carboxylate with ethyl 7-chloro-3,4,5,6-tetrahydrothieno[4,3,2-ef][3]benzazepine- 2-carboxylate, prepared as in Example 29, gave 7-chloro-3,4,5,6-tetrahydrothieno[4,3,2-ef][3]benzazepine-2-methanol: mp 184°-186° C.

Using the general procedure of Example 3, replacing 7-chloro-3,4,5,6-tetrahydro-4-methylthieno[4,3,2-ef][3]benzazepine-2-methanol with 7-chloro-3,4,5,6-tetrahydrothieno[4,3,2-ef][3]benzazepine-2-methanol gave 7-chloro-3,4,5,6-tetrahydrothieno[4,3,2-ef][3]benzazepine-2-carboxaldehyde: mp 120° C.

Using the general procedure of Example 4, replacing 7-chloro-3,4,5,6-tetrahydro-4-methylthieno[4,3,2-ef][3]benzazepine-2-carboxaldehyde with 7-chloro-3,4,5,6-tetrahydrothieno[4,3,2-ef][3]benzazepine-2-carboxaldehyde gave 7-chloro-2-ethenyl-3,4,5,6-tetrahydrothieno[4,3,2-ef][3]benzazepine hydrochloride: mp 210° C.

EXAMPLE 38

An oral dosage form for administering the presently invented compounds is produced by screening, mixing, and filling into a hard gelatin capsule ingredients in the proportions shown in Table II, below.

TABLE II

| Ingredients | Amounts |
| --- | --- |
| Ethyl (E)-3-(7-Chloro-3,4,5,6-tetrahydro-4-methylthieno[4,3,2-ef][3]benzazepin-2-yl)-2-propenoate | 50 mg |
| magnesium stearate | 5 mg |
| lactose | 75 mg |

EXAMPLE 39

The sucrose, calcium sulfate dihydrate and Formula (I) compound shown in Table III below, are mixed and granulated with a 10% gelatin solution. The wet granules are screened, dried, mixed with the starch, talc and stearic acid, screened and compressed into a tablet.

TABLE III

| Ingredients | Amounts |
| --- | --- |
| 7-Chloro-2-ethenyl-3,4,5,6 tetrahydro-4-methyl-thieno[4,3,2-ef][3]benzazepine | 100 mg |
| calcium sulfate dihydrate | 150 mg |
| sucrose | 20 mg |
| starch | 10 mg |
| talc | 5 mg |
| stearic acid | 3 mg |

EXAMPLE 40

7-Chloro-2-ethenyl-3,4,5,6-tetrahydro-4-methylthieno[4,3,2-ef][3]benzazepine hydrochloride, 75 mg, is dispersed in 25 ml of normal saline to prepare an injectable preparation.

Contemplated equivalents of Formula (I) compounds are compounds that upon administration to mammals, including humans, are metabolized to Formula (I) compounds or metabolized to any Formula (I) compound active metabolites at a sufficient rate and in sufficient amounts to produce physiologic activity of Formula (I) compounds. Such compounds also would be included in the invented pharmaceutical compositions and used in the invented methods.

While the preferred embodiments of the invention are illustrated by the above, the invention is not limited to the precise instructions herein disclosed and that the right to all modifications coming within the scope of the following claims is reserved.

What is claimed is:

1. A compound represented by the formula:

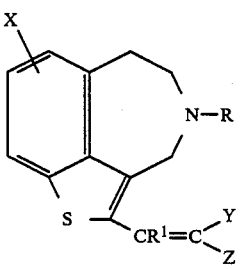

in which:
- X is H, Cl, Br, F, I, CF$_3$, C$_{1-6}$alkyl, COR$^{10}$, CO$_2$R$^{10}$, CONR$^{16}$R$^{11}$, CN, NO$_2$, NR$^{12}$R$^{13}$, OR$^{12}$, SC$_{1-4}$alkyl, S(CH$_2$)$_{0-6}$aryl, SCF$_3$, or any accessible combination thereof of up to three substituents;
- R is H, C$_{1-6}$alkyl, or C$_{3-5}$alkenyl;
- R$^1$ is H or C$_{1-6}$alkyl;
- R$^{10}$ is C$_{1-6}$alkyl or (CH$_2$)$_{0-6}$aryl;
- R$^{11}$ and R$^{16}$ independently are H, C$_{1-6}$alkyl, or (CH$_2$)$_{0-6}$aryl;
- R$^{12}$ is H, C$_{1-6}$alkyl, COR$^{14}$, or SO$_2$R$^{15}$;
- R$^{13}$ is H or C$_{1-6}$alkyl;
- R$^{14}$ and R$^{15}$ independently are C$_{1-6}$alkyl or (CH$_2$)$_{0-6}$aryl;
- Y and Z independently are H, NO$_2$, C$_{1-6}$alkyl, CH$_2$CH$_2$OH, CN, CH$_2$OR$^2$, CH$_2$SR$^2$, COR$^2$, CO$_2$R$^2$, CONR$^3$R$^4$, SO$_2$NR$^3$R$^4$, SO$_3$R$^2$, SO$_2$R$^5$, SOR$^5$, P(O)(OR$^3$)(OR$^4$), P(O)R$^5$(OR$^3$), P(O)R$^5$R$^6$, P(O)(OR$^2$)NR$^3$R$^4$, P(O)(NR$^3$R$^4$)$_2$, P(O)R$^5$(NR$^3$R$^4$), halo, CF$_3$, or (CH$_2$)$_{0-6}$aryl;
- R$^2$, R$^3$, and R$^4$ independently are H, C$_{1-6}$alkyl, C$_{3-5}$alkenyl, or (CH$_2$)$_{0-6}$aryl; and
- R$^5$ and R$^6$ independently are C$_{1-6}$alkyl, C$_{3-5}$alkenyl, or (CH$_2$)$_{0-6}$aryl; or a pharmaceutically acceptable salt thereof.

2. A compound of claim 1 having the formula:

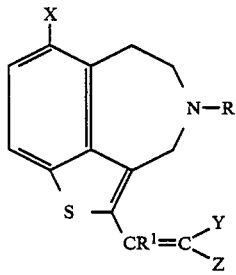

in which:
- X is H, Cl, Br, F, I, CF$_3$, C$_{1-6}$alkyl, COR$^{10}$, CO$_2$R$^{10}$, CONR$^{16}$R$^{11}$, CN, NO$_2$, NR$^{12}$R$^{13}$, OR$^{12}$, SC$_{1-46}$alkyl, S(CH$_2$)$_{0-6}$aryl, or SCF$_3$;
- R is H, C$_{1-6}$alkyl, or C$_{3-5}$alkenyl;
- R$^1$ is H or C$_{1-6}$alkyl;
- R$^{10}$ is C$_{1-6}$alkyl or (CH$_2$)$_{0-6}$aryl;
- R$^{11}$ and R$^{16}$ independently are H, C$_{1-6}$alkyl, or (CH$_2$)$_{0-6}$aryl;
- R$^{12}$ is H, C$_{1-6}$alkyl, COR$^{14}$, or SO$_2$R$^{15}$;
- R$^{13}$ is H or C$_{1-6}$alkyl;
- R$^{14}$ and R$^{15}$ independently are C$_{1-6}$alkyl or (CH$_2$)$_{0-6}$aryl;
- Y and Z independently are H, NO$_2$, C$_{1-6}$alkyl, CH$_2$CH$_2$OH, CN, CH$_2$OR$^2$, CH$_2$SR$^2$, COR$^2$, CO$_2$R$^2$, CONR$^3$R$^4$, SO$_2$NR$^3$R$^4$, SO$_3$R$^2$, SO$_2$R$^5$, SOR$^5$, P(O)(OR$^3$)(OR$^4$), P(O)R$^5$(OR$^3$), P(O)R$^5$R$^6$, P(O)(OR$^2$)NR$^3$R$^4$, P(O)(NR$^3$R$^4$)$_2$, P(O)R$^5$(NR$^3$R$^4$), halo, CF$_3$, or (CH$_2$)$_{0-6}$aryl;
- R$^2$, R$^3$, and R$^4$ independently are H, C$_{1-6}$alkyl, C$_{3-5}$alkenyl, or (CH$_2$)$_{0-6}$aryl; and
- R$^5$ and R$^6$ independently are C$_{1-6}$alkyl, C$_{3-5}$alkenyl, or (CH$_2$)$_{0-6}$aryl; or a pharmaceutically acceptable salt thereof.

3. A compound of claim 2 wherein X is Cl, Br, F, or I.

4. A compound of claim 3 wherein R is CH$_3$ or H.

5. A compound of claim 4 that is 7-chloro-2-ethenyl-3,4,5,6-tetrahydro-4-methylthieno[4,3,2-ef][3]benzazepine, or a pharmaceutically acceptable salt thereof.

6. A compound of claim 4 that is:
- ethyl (E)-3-(7-chloro-3,4,5,6-tetrahydro-4-methyl-thieno[4,3,2-ef][3]benzazepin-2-yl)-2-propenoate;
- ethyl (E)-3-(7-chloro-3,4,5,6-tetrahydro-4-methyl-thieno[4,3,2-ef][3]benzazepin-2-yl)-2-methyl-2-propenoate;
- (E)-3-(7-chloro-3,4,5,6-tetrahydro-4-methyl-thieno[4,3,2-ef][3]benzazepin-2-yl)-2-propenamide;
- (E)-3-(7-chloro-3,4,5,6-tetrahydro-4-methyl-thieno[4,3,2-ef][3]benzazepin-2-yl)-N-methyl-2-propenamide;
- (E)-3-(7-chloro-3,4,5,6-tetrahydro-4-methyl-thieno[4,3,2-ef][3]benzazepin-2-yl)-N,N-dimethyl-2-propenamide;
- (E)-3-(7-chloro-3,4,5,6-tetrahydro-4-methyl-thieno[4,3,2-ef][3]benzazepin-2-yl)-2-propen-1-ol;
- 7-chloro-2-ethenyl-3,4,5,6-tetrahydrothieno[4,3,2-ef][3]benzazepine;
- ethyl (E/Z)-3-(7-chloro-3,4,5,6-tetrahydro-4-methyl-thieno[4,3,2-ef][3]benzazepin-2-yl)-2-phenyl-2-propenoate;
- (E)-3-(7-chloro-3,4,5,6-tetrahydro-4-methyl-thieno[4,3,2-ef][3]benzazepin-2-yl)-2-phenyl-2-propenenitrile;
- 7-chloro-3,4,5,6-tetrahydro-4-methyl-2-(1-methylethenyl)thieno[4,3,2-ef][3]benzazepine; or
- 7-chloro-2-propenyl-3,4,5,6-tetrahydrothieno[4,3,2-ef][3]benzazepine;

or a pharmaceutically acceptable salt thereof.

7. A pharmaceutical composition comprising a compound of claim 1 and a suitable pharmaceutical carrier.

8. A pharmaceutical composition of claim 7 wherein the compound is 7-chloro-2-ethenyl-3,4,5,6-tetrahydro-4-methylthieno[4,3,2-ef][3]benzazepine.

9. A pharmaceutical composition of claim 7 wherein the compound is:
- ethyl (E)-3-(7-chloro-3,4,5,6-tetrahydro-4-methyl-thieno[4,3,2-ef][3]benzazepin-2-yl)-2-propenoate;
- ethyl (E)-3-(7-chloro-3,4,5,6-tetrahydro-4-methyl-thieno[4,3,2-ef][3]benzazepin-2-yl)-2-methyl-2-propenoate;
- (E)-3-(7-chloro-3,4,5,6-tetrahydro-4-methyl-thieno[4,3,2-ef][3]benzazepin-2-yl)-2-propenamide;
- (E)-3-(7-chloro-3,4,5,6-tetrahydro-4-methyl-thieno[4,3,2-ef][3]benzazepin-2-yl)-N-methyl-2-propenamide;
- (E)-3-(7-chloro-3,4,5,6-tetrahydro-4-methyl-thieno[4,3,2-ef][3]benzazepin-2-yl)-N,N-dimethyl-2-propenamide;
- (E)-3-(7-chloro-3,4,5,6-tetrahydro-4-methyl-thieno[4,3,2-ef][3]benzazepin-2-yl)-2-propen-1-ol;
- 7-chloro-2-ethenyl-3,4,5,6-tetrahydrothieno[4,3,2-ef][3]benzazepine;

ethyl (E/Z)-3-(7-chloro-3,4,5,6-tetrahydro-4-methylthieno[4,3,2-ef][3]benzazepin-2-yl)-2-phenyl-2-propenoate;

(E)-3-(7-chloro-3,4,5,6-tetrahydro-4-methylthieno[4,3,2-ef][3]benzazepin-2-yl)-2-phenyl-2-propenenitrile;

7-chloro-3,4,5,6-tetrahydro-4-methyl-2-(1-methylethenyl)thieno[4,3,2-ef][3]benzazepine; or 7-chloro-2-propenyl-3,4,5,6-tetrahydrothieno[4,3,2-ef][3]benzazepine.

10. A method of antagonizing α-adrenergic receptors in mammals that comprises administering to a subject in need thereof an effective amount of a compound of claim 1.

11. A method of claim 10 wherein the compound is 7-chloro-2-ethenyl-3,4,5,6-tetrahydro-4-methylthieno[4,3,2-ef][3]benzazepine.

12. A method of claim 10 wherein the compound is:
ethyl (E)-3-(7-chloro-3,4,5,6-tetrahydro-4-methylthieno[4,3,2-ef][3]benzazepin-2-yl)-2-propenoate;

ethyl (E)-3-(7-chloro-3,4,5,6-tetrahydro-4-methylthieno-[4,3,2-ef][3]benzazepin-2-yl)-2-methyl-2-propenoate;

(E)-3-(7-chloro-3,4,5,6-tetrahydro-4-methylthieno[4,3,2-ef][3]benzazepin-2-yl)-2-propenamide;

(E)-3-(7-chloro-3,4,5,6-tetrahydro-4-methylthieno[4,3,2-ef][3]benzazepin-2-yl)-N-methyl-2-propenamide;

(E)-3-(7-chloro-3,4,5,6-tetrahydro-4-methylthieno[4,3,2-ef][3]benzazepin-2-yl)-N,N-dimethyl-2-propenamide;

(E)-3-(7-chloro-3,4,5,6-tetrahydro-4-methylthieno[4,3,2-ef][3]benzazepin-2-yl)-2-propen-1-ol;

7-chloro-2-ethenyl-3,4,5,6-tetrahydrothieno[4,3,2-ef][3]benzazepine;

ethyl (E/Z)-3-(7-chloro-3,4,5,6-tetrahydro-4-methylthieno[4,3,2-ef][3]benzazepin-2-yl-2-phenyl-2-propenoate;

(E)-3-(7-chloro-3,4,5,6-tetrahydro-4-methylthieno[4,3,2-ef][3]benzazepin-2-yl-2-phenyl-2-propenenitrile;

7-chloro-3,4,5,6-tetrahydro-4-methyl-2-(1-methylethenyl)thieno[4,3,2-ef][3]benzazepine; or 7-chloro-2-propenyl-3,4,5,6-tetrahydrothieno[4,3,2-ef][3]benzazepine.

13. A method of reducing blood pressure in mammals that comprises administering to a subject in need thereof an effective amount of a compound of claim 1.

14. A method of treating benign prostatic hypertrophy in mammals that comprises administering to a subject in need thereof an effective amount of a compound of claim 1.

15. A method of treating peripheral vascular disease in mammals that comprises administering to a subject in need thereof an effective amount of a compound of claim 1.

16. A method of treating congestive heart failure in mammals that comprises administering to a subject in need thereof an effective amount of a compound of claim 1.

* * * * *